United States Patent [19]

King et al.

[11] 4,259,195

[45] Mar. 31, 1981

[54] REACTION PRODUCT OF ACIDIC MOLYBDENUM COMPOUND WITH BASIC NITROGEN COMPOUND AND LUBRICANTS CONTAINING SAME

[75] Inventors: John M. King, San Rafael; Louis deVries, Greenbrae, both of Calif.

[73] Assignee: Chevron Research Company, San Francisco, Calif.

[21] Appl. No.: 53,014

[22] Filed: Jun. 28, 1979

[51] Int. Cl.[1] ............................................. C10M 1/10
[52] U.S. Cl. .................................. 252/49.7; 252/25; 252/34.7; 252/46.4; 252/51
[58] Field of Search ................... 252/34.7, 46.4, 49.7, 252/51, 25

[56] References Cited

U.S. PATENT DOCUMENTS

| | | | |
|---|---|---|---|
| 3,140,997 | 7/1964 | Price | 252/25 X |
| 3,223,625 | 12/1965 | Cyphers et al. | 252/49.7 X |
| 3,281,355 | 10/1966 | Cyphers et al. | 252/25 X |
| 3,541,014 | 11/1970 | LeSuer | 252/25 X |

FOREIGN PATENT DOCUMENTS 796732  6/1958  United Kingdom ................... 252/49.7

*Primary Examiner*—Andrew Metz
*Attorney, Agent, or Firm*—S. R. LaPaglia; V. J. Cavalieri

[57] ABSTRACT

Antioxidant additives for lubricating oil are prepared by combining a polar promoter, an acidic molybdenum compound and certain basic nitrogen compound to form a molybdenum-containing compositions.

15 Claims, No Drawings

REACTION PRODUCT OF ACIDIC MOLYBDENUM COMPOUND WITH BASIC NITROGEN COMPOUND AND LUBRICANTS CONTAINING SAME

FIELD OF THE INVENTION

This invention relates to new lubricating oil compositions. More specifically, it relates to new lubricating oil compositions containing antioxidant molybdenum compounds.

BACKGROUND OF THE INVENTION

Molybdenum disulfide has long been known as a desirable additive for use in lubricating oil compositions. However, one of its major detriments is its lack of oil solubility. Molybdenum disulfide is ordinarily finely ground and then dispersed in the lubricating oil composition to impart friction modifying and antiwear properties. Finely ground molybdenum disulfide is not an effective oxidation inhibitor in lubricating oils.

As an alternative to finely grinding the molybdenum disulfide, a number of different approaches involving preparing salts of molybdenum compounds have been tried. One type of compound which has been prepared molybdenum dithiocarbamates. Representative compositions are described in U.S. Pat. No. 3,419,589, which teaches molybdenum (VI) dioxide dialkyldithiocarbamates; U.S. Pat. No. 3,509,051, which teaches sulfurized oxymolybdenum dithiocarbamates; and U.S. Pat. No. 4,098,705, which teaches sulfur containing molybdenum dihydrocarbyl dithiocarbamate compositions.

An alternative approach is to form dithiophosphates instead of dithiocarbamates. Representative of this type of molybdenum compound are the compositions described in U.S. Pat. No. 3,494,866, such as oxymolybdenum diisopropylphosphorodithioate.

U.S. Pat. No. 3,184,410 describes certain dithiomolybdenyl acetylacetonates for use in lubricating oils.

Braithwaite and Greene in Wear, 46 (1978) 405–432 decribe various molybdenum-containing compositions for use in motor oils.

U.S. Pat. No. 3,349,108 teaches a molybdenum trioxide complex with diethylenetriamine for use as an additive for molten steel.

Russian Pat. No. 533,625 teaches lube oil additives prepared from ammonium molybdate and alkenylated polyamines.

Another way to incorporate molybdenum compounds in oil is to prepare a colloidal complex of molybdenum disulfide or oxysulfides dispersed using known dispersants. U.S. Pat. No. 3,223,625 describes a procedure in which an acidic aqueous solution of certain molybdenum compounds is prepared and then extracted with a hydrocarbon ether dispersed with an oil soluble dispersant and then freed of the ether. U.S. Pat. No. 3,281,355 teaches the preparation of a dispersion of molybdenum disulfide by preparing a mixture of lubricating oil, dispersant, and a molybdenum compound in water or $C_{1-4}$ aliphatic alcohol, contacting this with a sulfide ion generator and then removing the solvent. Dispersants noted to be effective in this procedure are petroleum sulfonates, phenates, alkylphanate sulfides, phosphosulfurized olefins and combinations thereof.

SUMMARY OF THE INVENTION

It has now been found that a lubricating oil additive can be prepared by combining a polar promoter, an acidic molybdenum compound and certain basic nitrogen-containing compositions.

DETAILED DESCRIPTION OF THE INVENTION

Lubricating oil compositions containing the additive disclosed herein are effective as either fluid and grease compositions (depending upon the specific additive or additives employed) for inhibiting oxidation, imparting antiwear and extreme pressure properties, and modifying the friction properties of the oil which may, when used as a crankcase lubricant, lead to improved mileage for the vehicle being lubricated with a lubricating oil of this invention.

The precise molecular formula of the molybdenum compositions prepared in the process of this invention is not known with certainty; however, they are believed to be compounds in which molybdenum, whose valences are satisfied with atoms of oxygen or sulfur is either complexed by or the salt of one or more nitrogen atoms of the basic nitrogen containing composition used in the preparation of these additives.

The molybdenum compounds used to prepare the additives for compositions of this invention are acidic molybdenum compounds. By acidic is meant that the molybdenum compounds will react with a basic nitrogen compound as measured by ASTM test D-664 or D-2896 titration procedure. Typically these molybdenum compounds are hexavalent and are represented by the following compositions: molybdic acid, ammonium molybdate, sodium molybdate, potassium molybdate and other alkali metal molybdates and other molybdenum salts such as $MoOCl_4$, $MoO_2Br_2$, $Mo_2O_3Cl_6$, molybdenum trioxide or similar acidic molybdenum compounds. Preferred acidic molybdenum compounds are molybdic acid, ammonium molybdate, and alkali metal molybdates. Particularly preferred are molybdic acid and ammonium molybdate.

The polar promoter used in the process of this invention is one which facilitates the interaction between the acidic molybdenum compound and the basic nitrogen compound. A wide variety of such promoters may be used. Typical promoters are 1,3-propanediol, 1,4-butanediol, diethylene glycol, butyl cellosolve, propylene glycol, 1,4-butyleneglycol, methyl carbitol, ethanolamine, diethanolamine, N-methyl-diethanol-amine, dimethyl formamide, N-methyl acetamide, dimethyl acetamide, methanol, ethylene glycol, dimethyl sulfoxide, hexamethyl phosphoramide, tetrahydrofuran and water. Preferred are water and ethylene glycol. Particularly preferred is water.

While ordinarily the polar promoter is separately added to the reaction mixture, it may also be present, particularly in the case of water, as a component of non-anhydrous starting materials or as waters of hydration in the acidic molybdenum compound, such as $(NH_4)_6Mo_7O_{24}.4H_2O$. Water may also be added as ammonium hydroxide.

The basic nitrogen compounds are selected from those having a basic nitrogen content as measured by ASTM D-664 or D-2896. It is preferred that they be oil-soluble. These composition are selected from succinimides, carboxylic acid amides, Mannich bases, phosphonamides, thiophosphoramides, dispersant viscosity index improvers, and mixtures thereof. These basic nitrogen containing compounds are described below (keeping in mind the reservation that each must have at least one basic nitrogen). Any of the nitrogen-containing compositions may be after-treated with e.g., boron, using procedures well known in the art so long as the after-treated product continues to contain basic nitrogen. These after-treatments are particularly applicable to succinimides and Mannich base compositions.

The mono and polysuccinimides that can be used to prepare the lubricating oil additives described herein are disclosed in numerous references and are well known in the art. Certain fundamental types of succinimides and the related materials encompassed by the term of art "succinimide" are taught in U.S. Pat. Nos. 3,219,666, 3,172,892, and 3,272,746, the disclosures of which are hereby incorporated by reference. The term succinimide is understood in the art to include many of the amide, imide, and amidine species which are also formed by this reaction. The predominant product, however, is a succinimide and this term has been generally accepted as meaning the product of a reaction of an alkenyl substituted succinic acid or anhydride with a nitrogen containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amine being especially characterized by ethylene diamine, diethylamine triamine, triethylene tetraamine, and tetraethylene pentamine. Particularly peferred are those succinimides prepared from polyisobutyl succinic anhydride of 70 to 128 carbon atoms and tetraethylene pentaamine or triethylene tetraamine or mixtures thereof.

Also included within the term succinimide are the cooligomers of a hydrocarbyl succinic acid or anhydride and a poly secondary amine containing at least one tertiary amino nitrogen in addition to two or more secondary amino groups. Ordinarily this composition has between 1,500 and 50,000 average molecular weight. A typical compound would be that prepared by reacting polyisobutenyl succinic anhydride and ethylene dipiperazine. Compositions of this type are disclosed in U.S. application Ser. No. 816,063, filed July 15, 1977 the disclosure of which is hereby incorporated by reference.

Carboxylic amide compositions are also suitable starting materials for preparing the products of in this invention. Typical of such compounds are those disclosed in U.S. Pat. No. 3,405,064, the disclosure of which is hereby incorporated by reference. These compositions are ordinarily prepared by reacting a carboxylic acid or anhydride ester thereof, having at least 12 to about 350 aliphatic carbon atoms in the principal aliphatic chain and, if desired, having pendant aliphatic groups to render the molecule oil soluble which is with an amine or a hydrocarbyl polyamine, such as an ethylene amine, to give a mono or polycarboxylic acid amide. Preferred are those amides prepared from (1) a carboxylic acid of the formula $R^2COOH$, where $R^2$ is $C_{12-20}$ alkyl or a mixture of this acid with a polyisobutenyl carboxylic acid in which the polyisobutenyl group contains from 72 to 128 carbon atoms and (2) an ethylene amine, especially triethylene tetraamine or tetraethylene pentaamine or mixtures thereof.

Another class of compounds useful for supplying basic nitrogen are the Mannich base compositions. The Mannich base compositions are prepared from a phenol or $C_{9-200}$ alkylphenol, an aldehyde, such as formaldehyde or formaldehyde precursor such a para-formaldehyde, and an amine compound. The amine may be a mono or polyamine and typical compositions are prepared from an alkylamine, such as methylamine, or an ethylene amine, such as diethylene triamine, or tetraethylene pentaamine and the like. The phenolic material may be sulfurized and preferably in dodecylphenol or a $C_{80-100}$ alkylphenol. Typical Mannich bases which can be used in this invention are disclosed in U.S. Pat. No. 4,157,309 and U.S. Pat. Nos. 3,649,229, 3,368,972 and 3,539,663, the disclosures of which are hereby incorporated by reference. The last application discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1-10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the composition.

The phosphoramides and phosphonamides, such as those disclosed in U.S. Pat. Nos. 3,909,430 and 3,968,157 the disclosures of which are hereby incorporated by reference, may be prepared by forming oil soluble phosphorus compound having at least one P-N bond. They can be prepared, for example, by reacting phosphorus oxychloride with a hydrocarbyl diol in the presence of a monoamine or by reacting phosphorus oxychloride with a difuctional secondary amine and a mono-functional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and nitrogen-containing compound as defined above, particularly an alkylamine, alkyldiamine, alkylpolyamine, or an alkyleneamine, such as ethylene diamine, diethylenetriamine, triethylenetetraamine, tetraethylenepentaamine, and the like.

Another class of nitrogen-containing compositions useful in preparing the molybdenum compositions of this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound, especially those nitrogen-containing compounds and compositions described herein. Preferred nitrogen sources are alkylene amines, such as ethylene amines, alkyl amines, and Mannich bases.

Preferred basic nitrogen compounds for use in this invention are succinimides, carboxylic acid amides, and Mannich bases.

The process of this invention may be carried out by combining the acidic molybdenum precursor as described above, in the presence of a polar promoter, with a basic nitrogen-containing composition as described above. The reaction is ordinarily carried out at atmospheric pressure; however, higher or lower pressures may be used, if desired, using methods that are well-known to those skilled in the art. A diluent may be used to enable the reaction mixture to be efficiently stirred. Typical diluents are lubricating oil and liquid compounds containing only carbon and hydrogen. If the mixture is sufficiently fluid to permit stirring, no diluent is necessary. A diluent which does not react with the molybdenum containing compound is desirable.

In the reaction mixture, the ratio of molybdenum compound to basic nitrogen compound is not critical; however, as the amount of molybdenum with respect to basic nitrogen, increases, the filtration of the product becomes more difficult. Since the molybdenum component probably oligomerizes, it is advantageously to add as much molybdenum as can easily be maintained in the composition. Usually the reaction mixture will have charged it from 0.01 to 2.00 atoms of molybdenum per basic nitrogen atom. Preferably from 0.4 to 1.0, and most preferably from 0.4 to 0.7, atoms of molybdenum per atom of basic nitrogen is added to the reaction mixture.

The polar promoter, which is preferably water, is ordinarily present in the ratio of 0.1 to 50 mols of water per mol of molybdenum. Preferably from 0.5 to 25 and most preferably 1.0 to 15 mols of the promoter is present per mol of molybdenum.

The lubricating oil compositions of this invention can be prepared by admixing, by conventional techniques, the appropriate amount of the molybdenum-containing composition with a lubricating oil. The selection of the particular base oil depends on the contemplated application of the lubricant and the presence of other additives. Generally, the amount of the molybdenum containing additive will vary from 0.05 to 15% by weight and preferably from 0.2 to 10% by weight.

The lubricating oil which may be used in this invention includes a wide variety of hydrocarbon oils, such as naphthenic bases, paraffin bases and mixed base oils as well as synthetic oils such as esters and the like. The lubricating oils may be used individually or in combination and generally have a viscosity which ranges from 50 to 5,000 SUS and usually from 100 to 15,000 SUS at 38° C.

In many instances, it may be advantageous to form concentrates of the molybdenum containing additive within a carrier liquid. These concentrates provide a convenient method of handling and transporting the additives before their subsequent diluted and use. The concentration of the molybdenum-containing additive within the concentrate may vary from 0.25 to 90% by weight although it is preferred to maintain a concentration between 1 and 50% by weight. The final application of the lubricating oil compositions of this invention may be in marine cylinder lubricants as in crosshead diesel engines, crankcase lubricants as in automobiles and railroads, lubricants for heavy machinery such as steel mills and the like, or as greases for bearings and the like. Whether the lubricant is fluid or a solid will ordinarily depend on whether a thickening agent is present. Typical thickening agents include polyurea acetates, lithium stearate and the like.

If desired, other additives may be included in the lubricating oil compositions of this invention. These additives include antioxidants or oxidation inhibitors, dispersants, rust inhibitors, anticorrosion agents and so forth. Also anti-foam agents stabilizers, anti-stain agents, tackiness agents, anti-chatter agents, dropping point improvers, anti-squawk agents, extreme pressure agents, odor control agents and the like may be included.

Certain molybdenum products that can be prepared by the process of invention also find utility in making brake lining materials, in high-temperature structural materials, in iron and steel alloys, in cladding materials, in electroplating solutions, as components for electrical discharge machine electrodes, as fuel additives, in making self-lubricating or wear-resistant structures, as mold release agents, in compositions for phosphatizing steel, in brazing fluxes, in nutrient media for microorganisms, in making electrosensitive recording material, in catalysts for refining coal, oil, shale, tar sands, and the like or as stabilizers or curing agents for natural rubber or polymers.

The following examples are presented to illustrate the operation of the invention and are not intended to be a limitation upon the scope of the claims.

EXAMPLE 1

To a 1 liter flask was added 290 grams of a solution of 45% concentrate in oil of the succinimide prepared from polyisobutenyl succinic anhydride and tetraethylene pentaamine and having a number average molecular weight for the polyisobutenyl group of about 980, 28.8 grams of molybdenum trioxide as a dry powder, 9.6 ml of water and 150 ml of hydrocarbon thinner. The reaction mixture, which was a murky yellow-green suspension, was heated to 65° C. and held at this temperature for 3½ hours. The temperature was then raised to 150° C. to remove water and held at this temperature for one hour. Then 50 ml of hot hydrocarbon thinner was added and the reaction mixture was filtered through diatomaceous earth. The filter cake was washed with 100 ml of hot hydrocarbon thinner and a light blue residue remained on the filter cake. The reaction mixture was then stripped to 160° C. at 20 mm Hg to yield a product containing 4.16% molybdenum, 3.48% oxygen, and 1.97% nitrogen.

EXAMPLE 2

To a 1-liter flask was added 290 grams of the succinimide described in Example 1 and 150 ml of hydrocarbon thinner. The mixture was heated to 65° C. and then 28.8 grams of molybdenum trioxide and 50 ml of water was added. The temperature of the mixture was maintained at 65° C. for ½ hour and then increased to 155° C. over a period of one hour and maintained at 155° C. to 160° C. for one hour. To this mixture was added 50 ml hydrocarbon thinner and the product was filtered through diatomaceous earth. The filtrate was stripped to 160° C. at 20 mm Hg to yield 311 grams of product containing 6.18% molybdenum, 4.17% oxygen and 1.94% nitrogen.

EXAMPLE 3

To a 3-liter flask was added 1160 g of the succinimide described in Example 1 and 800 ml hydrocarbon thinner. The temperature of the mixture was increased to 75° C. and 200 ml water and 116 g MoO3 were added and the mixture was stirred at 97° C. for 3 hours. It was then stripped at 188° C. After cooling to 130° C., 100 ml hydrocarbon thinner and 25 g diatomaceous earth were added and the mixture was filtered through diatomaceous earth and then stripped at 180° C. and 20 mm Hg. The product contained 5.84% molybdenum and 1.92% nitrogen.

EXAMPLE 4

To a 1-liter flask containing 290 g of the succinimide described in Example 1 and 200 ml hydrocarbon thinner at 65° C. was added 50 ml water and 58 g MoO3. The mixture was stirred at reflux for 4.5 hours and then stripped at 198°–209° C. The product was diluted with hydrocarbon thinner and then filtered through diatomaceous earth to yield 332 g of product containing 10.1% molybdenum (by X-ray fluorescence), 9.71% molybdenum (by neutron activation) and 5.97% oxygen (by neutron activation).

EXAMPLE 5

Lubricating oil compositions containing the additives prepared according to this invention have been tested in a variety of tests. Reported below are results from certain of these tests which are described as follows.

In the Oxidator B test the stability of the oil is measured by the time required for the consumption of 1 liter of oxygen by 100 grams of the test oil at 340° F. In the actual test, 25 grams of oil is used and the results are corrected to 100-gram samples. The catalyst which is used at a rate of 1.38 cc per 100 cc oil contains a mixture of soluble salts providing 95 ppm copper, 80 ppm iron, 4.8 ppm manganese, 1100 ppm lead, and 49 ppm tin. The results of this test are reported as hours to consumption of 1 liter of oxygen and our measure of the oxidative stability of the oil.

The anti-corrosion properties of compositions can be tested by their performance in the CRC L-38 bearing corrosion test. In this test, separate strips of copper and lead are immersed in the test lubricant and the lubricant is heated for 20 hours at a temperature of 295° F. The copper strip is weighed and then washed with potassium cyanide solution to remove copper compound deposits. It is then re-weighed. The weight losses of the two strips are reported as a measure of the degree of corrosion caused by the oil.

The copper strip test is a measure of corrosivity toward non-ferrous metals and is described as ASTM Test Method D-130. Anti-wear properties are measured by the 4-ball wear and the 4-ball weld tests. The 4-ball wear test is described in ASTM D-2266 and the 4-ball weld test is ASTM D-2783. The data for some of the tests run on compositions of this invention is reported in the Table below. The coefficient of friction of lubricating oils containing additives of this invention was tested in the Kinetic Oiliness Testing Machine (KOTM) manufactured by G. M. Neely of Berkeley, California. The procedure used in this test is described by G. L. Neely, Proceeding of Mid-Year Meeting, American Petroleum Institute 1932, pp. 60–74 and in ASLE Transactions, Vol. 8, pages 1–11 (1965 and ASLE Transactions, Vol. 7, pages 24–31 (1964). The coefficient of friction was measured under boundary conditions at 150° and 204° C. using a 1 Kg load and a molybdenum-filled ring on a cast-iron disk.

The formulations tested contained, in neutral oil, 3.5% of a 50% in oil solution of succinimide, 22 mmols/kg of the molybdenum product being tested, 20 mmols/kg sulfurized calcium phenate, 30 mmols/kg overbased magnesium sulfonate, 5.5% viscosity index improver and, if necessary, additional succinimide to bring the total nitrogen content of the finished oil to 2.14%.

TABLE

| Product of Example | Oxidator B, hrs. | ASTM D-2266, mm | ASTM D-2783 kg | L-38 Cu, mg | L-38 Pb, mg | D-130 | Coefficient of Friction 150° C. | Coefficient of Friction 204° C. |
|---|---|---|---|---|---|---|---|---|
| 1 | 7.7 | .39 | 165 | 16.3 | 10.1 | | | |
| 2 | 8.0 | | | | | | | |
| 3 | 8.5 | | | | | 1A[1] | | |
| 4 | | | | | | | | |

[1]Formulation tested was 4% wt. molybdenum compound in neutral oil.

What is claimed is:

1. A process for preparing a molybdenum-containing composition which comprises reacting an acidic molybdenum compound selected from the group consisting of molybdic acid, ammonium molybdate, alkali metal molybdate, bromide and chloride molybdenum salts, and molybdenum trioxide and a basic nitrogen compound selected from the group consisting of a succinimide, carboxylic acid amide, Mannich Base, phosphonamide, thiophosphonamide, phosphoramide, and a hydrocarbon dispersant viscosity index improver wherein from 0.01 to 2 atoms of molybdenum are present per basic nitrogen atom, in the presence of a polar promoter wherein from 0.01 to 50 mols of promoter are present per mol of molybdenum, to form a molybdenum-containing complex.

2. The process of claim 1 wherein the acidic molybdenum compound is selected from molybdic acid, ammonium molybdate, and alkali metal molybdates.

3. The process of claim 2 wherein said acidic molybdenum compound is molybdic acid or ammonium molybdate, and said basic nitrogen compound is a carboxylic acid amide, or a Mannich base prepared a $C_{9-200}$ alkylphenol, formaldehyde, and an amine.

4. The process of claim 3 wherein said basic nitrogen compound is a carboxylic acid amide prepared from on or more carboxylic acids of the formula $R^2$-COOH, wherein $R^2$ is $C_{12-350}$ alkyl or $C_{12-350}$ alkenyl and a hydrocarbyl polyamine.

5. The process of claim 4 wherein $R^2$ is $C_{12-20}$ alkyl or $C_{12-20}$ alkenyl and the hydrocarbyl polyamine is tetraethylene pentaamine or triethylene tetraamine.

6. The process of claim 3 wherein said basic nitrogen compound is the Mannich base prepared from dodecyl phenol, formaldehyde, and methylamine.

7. The process of claim 3 wherein said Mannich base is prepared from a $C_{80-100}$ alkylphenol, formaldehyde, and triethylene tetraamine, tetraethylene pentaamine, or mixtures thereof.

8. The process of claim 1, 2, 3, 4, 5, 6, or 7 wherein said polar promoter is water.

9. The product prepared by the process of claims 1, 2, 3, 4, 5, 6, or 7.

10. The product prepared by the process of claim 8.

11. A lubricating oil composition comprising an oil of lubricating viscosity and from 0.05 to 15% by weight of the product of claim 9.

12. A lubricating oil concentrate composition comprising an oil of lubricating viscosity and from 15 to 90% by weight of the product of claim 9.

13. A lubricating oil composition comprising an oil of lubricating viscosity and from 0.05 to 15% by weight of the product of claim 10.

14. A lubricating oil concentrate composition comprising an oil of lubricating viscosity and from 15 to 90% by weight of the product of claim 10.

* * * * *

UNITED STATES PATENT AND TRADEMARK OFFICE
CERTIFICATE OF CORRECTION

PATENT NO. : 4,259,195
DATED : March 31, 1981
INVENTOR(S) : John M. King and Louis deVries It is certified that error appears in the above-identified patent and that said Letters Patent are hereby corrected as shown below:

Column 1, line 67, "alkylphanate" should read --alkylphenate--.

Column 4, line 36, "difuctional" should read --difunctional--.

Column 5, line 57, "diluted" should read --dilution--.

Signed and Sealed this

Twenty-first Day of July 1981

[SEAL]

Attest:

GERALD J. MOSSINGHOFF

Attesting Officer       Commissioner of Patents and Trademarks